United States Patent [19]
Cover et al.

[11] Patent Number: 5,899,884
[45] Date of Patent: May 4, 1999

[54] SUCTION REGULATOR

[75] Inventors: Reid S. Cover, Mountain View; Marius Popescu, San Jose, both of Calif.

[73] Assignee: Stryker Corporation, Kalamazoo, Mich.

[21] Appl. No.: 08/784,368

[22] Filed: Jan. 17, 1997

[51] Int. Cl.$^6$ .................................................. A61M 1/00
[52] U.S. Cl. ................................................. 604/119; 604/902
[58] Field of Search ......................... 604/118, 119, 604/902, 283, 246, 249, 30, 33, 313, 315, 316

[56] References Cited

U.S. PATENT DOCUMENTS

| | | |
|---|---|---|
| 1,313,105 | 8/1919 | Moran . |
| 3,395,705 | 8/1968 | Hamilton .................... 604/119 |
| 3,645,497 | 2/1972 | Nyboer ................... 604/119 X |
| 3,834,388 | 9/1974 | Sauer . |
| 4,205,677 | 6/1980 | Engstrom .................... 604/119 |
| 4,356,823 | 11/1982 | Jackson . |
| 4,430,073 | 2/1984 | Bemis et al. ................. 604/119 |
| 4,878,900 | 11/1989 | Sundt ....................... 604/902 X |
| 5,000,175 | 3/1991 | Pue . |
| 5,013,300 | 5/1991 | Williams ................... 604/902 X |
| 5,269,768 | 12/1993 | Cheung ...................... 604/119 |
| 5,531,712 | 7/1996 | Malcolm et al. . |

OTHER PUBLICATIONS

Arthrex Catalog Abstract for Model AR–6600 Suction Regulator (1 page).

Primary Examiner—Wynn Wood Coggins
Assistant Examiner—Sharon Finkel
Attorney, Agent, or Firm—Flynn, Thiel, Boutell & Tanis, P.C.

[57] ABSTRACT

A suction regulator having an elongated hollow body with interconnected distal and proximal ports at opposite ends thereof, each adapted to be connected to an end of a flexible conduits The proximal port is adapted for conduit connection to a vacuum source and the distal port is adapted for conduit connection to a device needing suction control. An elongated slot is provided in the hollow body and extends through a wall of the hollow body. The slot has converging straight side walls extending over a majority of a length of the slot and from a wide end to a narrow end thereof. The hollow body is provided with an axially extending guideway thereon which is operatively connected to the gate member and a guide structure thereon for guiding the gate member axially relative to the hollow body between a first position oriented spaced from the wide end of the slot so as to provide unobstructed access to the slot to thereby effect a minimum suction rate at the distal port and a second position fully obstructing access to the slot to thereby effect a maximum suction rate at the distal port.

29 Claims, 5 Drawing Sheets

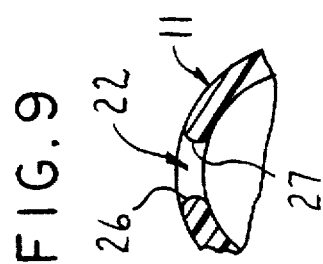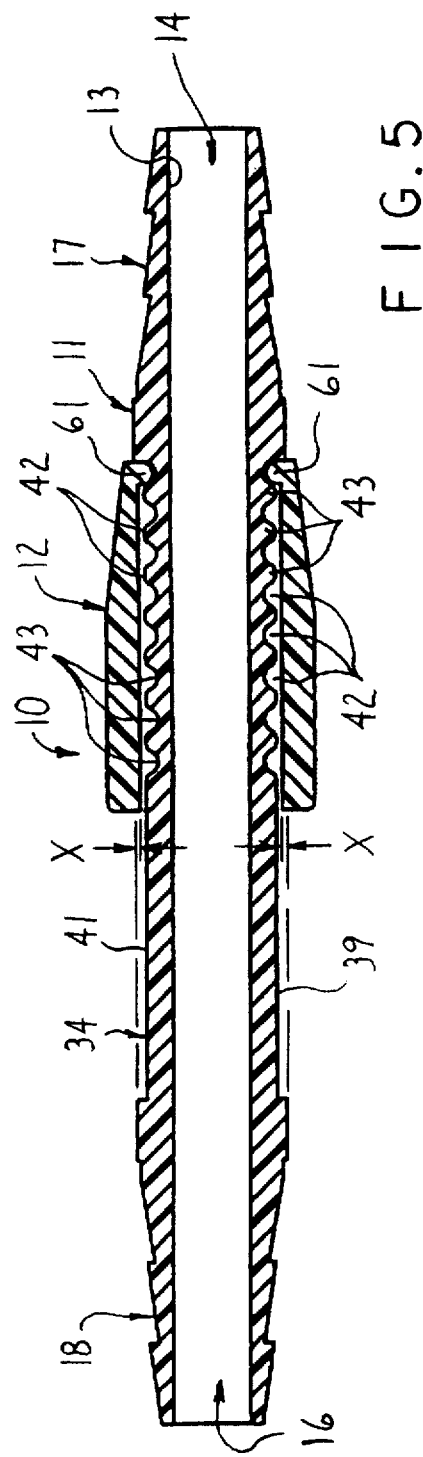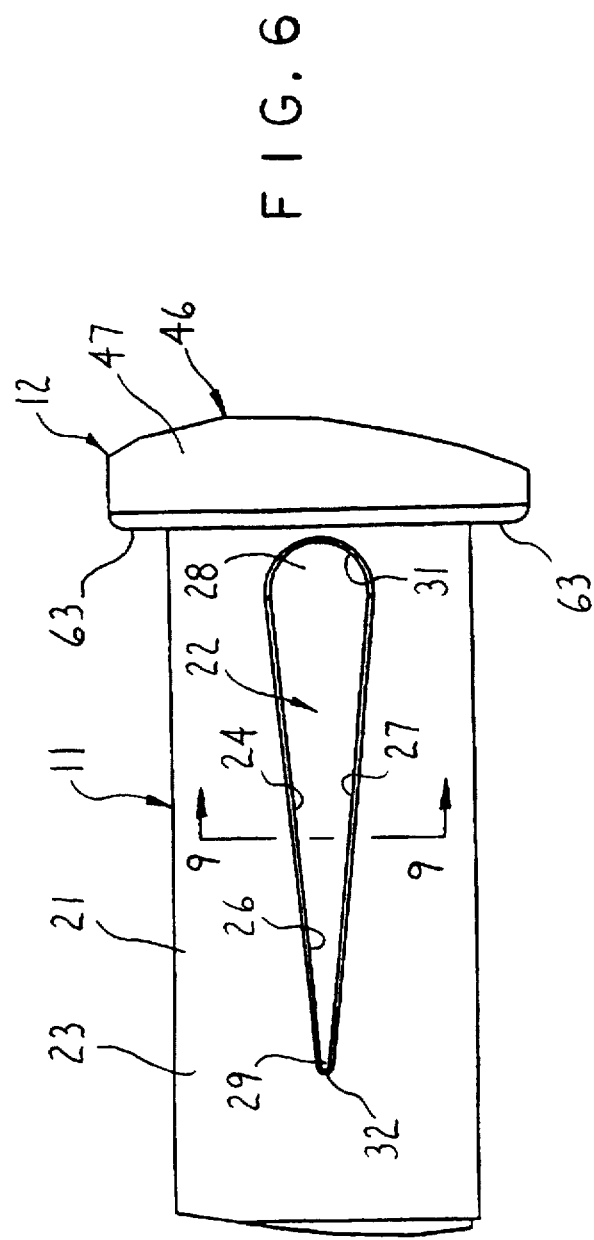

SUCTION REGULATOR

FIELD OF THE INVENTION

This invention relates to a suction regulator and, more particularly, to a surgical suction regulator for controlling the suction rate of a device needing suction control.

BACKGROUND OF THE INVENTION

During Arthroscopic, ENT, OB/GYN, Laparoscopic or any other surgical procedure, suction regulators are used to control the suction rate when removing bodily liquids or any other liquid which tends to collect in an area during a surgical procedure. The suction regulator device is connected in series with flexible tubing extending from a suction source, such as a hospital vacuum or suction canister, to a suction tip or any device needing control of suction. In many cases, it has been found that by installing a small suction regulator in series with the suction tip device, the flow in liters per minute can be regulated by letting a small amount of air into the tubing, therefore reducing the amount of suction force at the tip of the suction device.

One of the difficulties of constructing an effective control unit is to provide a passageway for liquid flow without reducing the diameter of the flow pathway. Liquids being drawn through the device frequently contain material that can block or clog the control unit. As a result, units of this type have heretofore provided large passageways which will not likely become obstructed even by a valve or even by a change in the direction of fluid flow.

One type of suction control device is disclosed in U.S. Pat. No. 5,000,175. The suction flow rate is regulated by positioning the operator's finger over an air intake. This type of device controls the air being drawn into the suction tube and, therefore, controls the rate of suction through the suction tube. This device does not, however, control the flow if the operator is absent or if the air intake is not closed off by the operator's finger. In other words, when the operator is not present, the suction rate falls to zero.

Another type of suction control device is disclosed in U.S. Pat. No. 4,356,823. The suction flow rate is controlled in a manner similar to the aforementioned U.S. Pat. No. 5,000, 175 but it cannot regulate the suction force over a wide and controlled range.

A still further suction regulator is disclosed in U.S. Pat. No. 5,531,712. In this device, the suction rate is regulated by screwing a plunger into an opening to shut off or open up the air flow to thereby regulate the suction rate.

None of the aforesaid devices, including an Arthrex Model AR-6600 suction regulator, is capable of linearly controlling the suction rate so as to enable the user thereof to manipulate and control the suction force at the device needing suction control, such as a suction tip device used in surgical procedures. This becomes important during surgical procedures where the surgeon is desirous of having liquid or loose tissue removed from delicate regions where it is necessary to increase the suction rate ever so gradually so as not to disturb the surrounding area of the surgical site.

Accordingly, it is the object of the present invention to provide a suction regulator having an elongated hollow body which has therein an elongated slot in the wall thereof which is of an asymmetrical configuration so that when a gate member slides with respect thereto to either open or close off a portion of the slot, the suction rate at a distal end of the suction regulator is controlled in a linear manner.

It is a further object of the invention to provide a suction regulator, as aforesaid, wherein the elongated slot includes converging side walls extending over a majority of the length of the slot and from a wide end to a narrow end in an axial direction of the hollow body so that when the gate member slides with respect thereto, portions of the slot will be covered so as to effect the aforesaid linear control of the suction rate.

It is a further object of the invention to provide a suction regulator, as aforesaid, wherein the converging side walls are straight over a majority of the length of the slot.

It is a further object of the invention to provide a suction regulator, as aforesaid, wherein a guide structure is provided for facilitating a tactile indexing of the gate member to selected positions whereat the gate member is yieldably held until a manual force applied by the user occurs to cause the gate member to move with respect to the hollow body.

It is a further object of the invention to provide a suction regulator, as aforesaid, wherein the components are made of a metal or synthetic resin material and, if of a synthetic resin material, by an injection molding process.

It is a further object of the invention to provide a suction regulator, as aforesaid, wherein the side wall are smooth and rounded so as to minimize air nose.

It is a further object of the invention to provide a suction regulator, as aforesaid, wherein the components can be quickly and easily assembled with a minimum of instruction.

It is a further object of the invention to provide a suction regulator, as aforesaid, wherein the suction regulator is of a durable construction and is reliably operable with a minimum of instruction and is maintenance free.

SUMMARY OF THE INVENTION

The objects and purposes of the invention have been met by providing a suction regulator which includes an elongated hollow body having interconnected distal and proximal ports at opposite ends thereof adapted to be connected to an end of a flexible conduit, the proximal port being adapted for conduit connection to a vacuum source and the distal port being adapted for conduit connection to a device needing suction control. An elongated slot is provided in the hollow body and extends through a wall of the hollow body. The slot has converging side walls extending over a majority of a length of the slot and from a wide end to a narrow end thereof. The hollow body is provided with an axially extending guideway thereon which operatively guides a gate member and a guide structure thereon for axially relative to the body between a first position oriented spaced from the wide end of the slot so as to provide unobstructed access to the slot to thereby effect a minimum suction rate at the distal port and a second position fully obstructing access to the slot to thereby effect a maximum suction rate at the distal port.

BRIEF DESCRIPTION OF THE DRAWINGS

Further objects and purposes of the invention will become apparent to persons acquainted with suction regulators by referencing the following text and accompanying drawings, in which:

FIG. 5 is a sectional view taken along the line 5—5 of FIG. 2;

FIG. 6 is an enlarged fragment of the top view illustrated in FIG. 3;

FIG. 9 is a sectional view taken along the line 9—9 of FIG. 6.

DETAILED DISCUSSION

Figure 7:
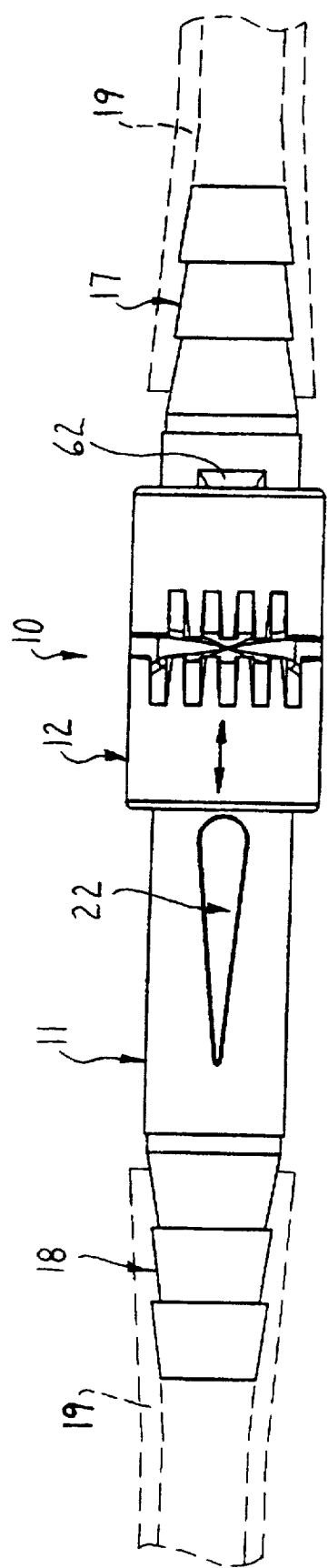
FIG. 7 is a view like FIG. 3, but with suction tubing shown in broken lines.

The suction regulator 10 includes a hollow body 11 and a gate member 12 slidably disposed on the hollow body. The hollow body 11 has a central bore extending therethrough terminating in a proximal port 14 and a distal port 16. Conventional tubular feedings 17 and 18 are provided at the proximal and distal ports, respectively, to facilitate engagement into flexible plastic tubes 19 (FIG. 7) or the like. The region between the tubular feedings 17 and 18 is generally cylindrical in construction with the upper half of the outer surface 23 of the cylinder 21 being smooth and cylindrical in nature. The region of the upper half 21 of the hollow body 11 closest to the distal port 16 and the tubular feedings 18 includes an elongated slot 22 extending from the exterior surface 23 of the hollow body 11 through the wall 24 so as to communicate with the central bore 13. In this particular embodiment, the side walls 26 and 27 of the elongated slot 22 are, in this embodiment, straight and converge from a wide end 28 to a narrow end 29 thereof. In this particular embodiment, the wide end of the slot is curved as at 31 about a uniform radius having a centerpoint located within the slot 22. Similarly, the narrow end of the slot is curved as at 32 about a further uniform radius having a centerpoint located within the slot 22. The purpose of the aforesaid configuration of the slot 22 will be set forth in more detail below. As shown in FIG. 9, the side wall 26 and 27 each have a smooth and rounded convex surface so that air flowing past and over the surface will do so quietly. The wall at the wide end and the narrow end of the slot also have a smooth and convex surface configuration.

Figure 1:
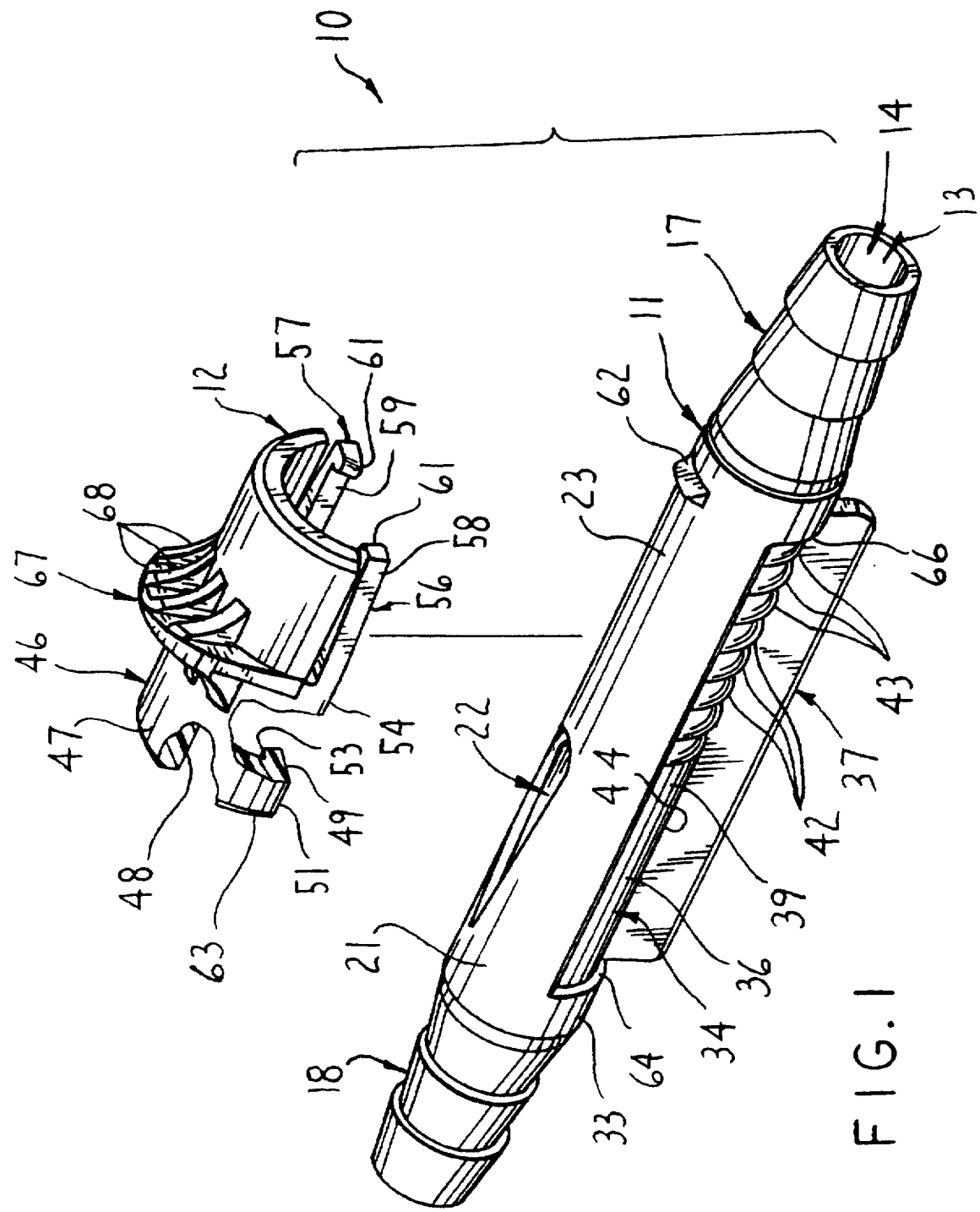
FIG. 1 is an isometric view of a suction regulator embodying the invention.
Figure 2:
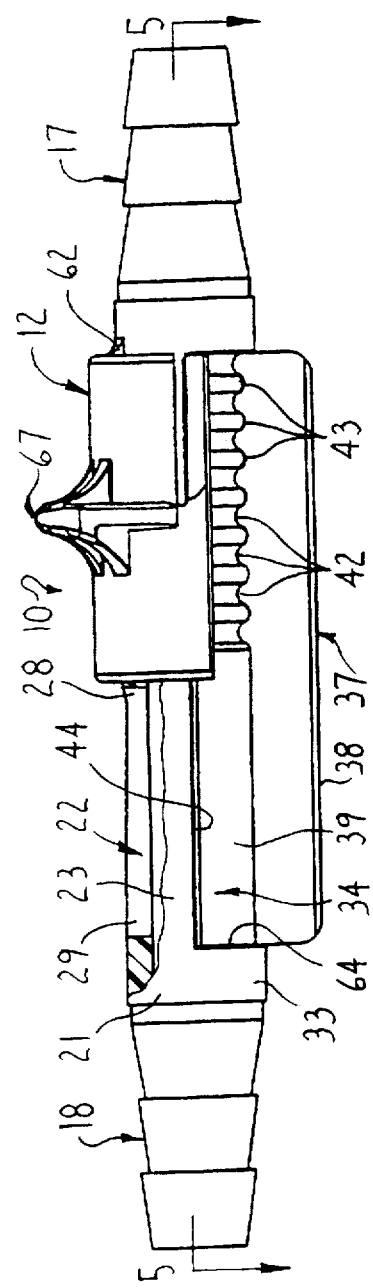
FIG. 2 is a front view of the suction regulator.
Figure 3:
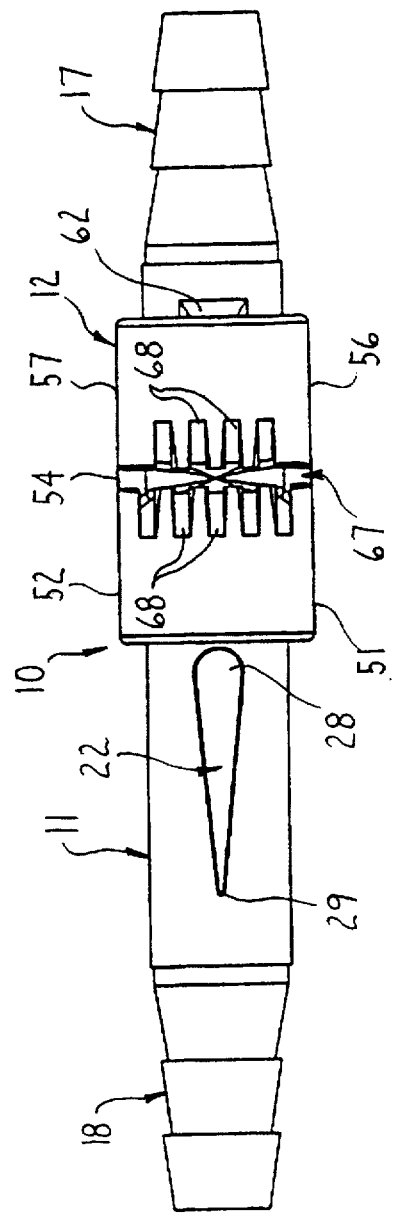
FIG. 3 is a top view of the suction regulator.
Figure 4:
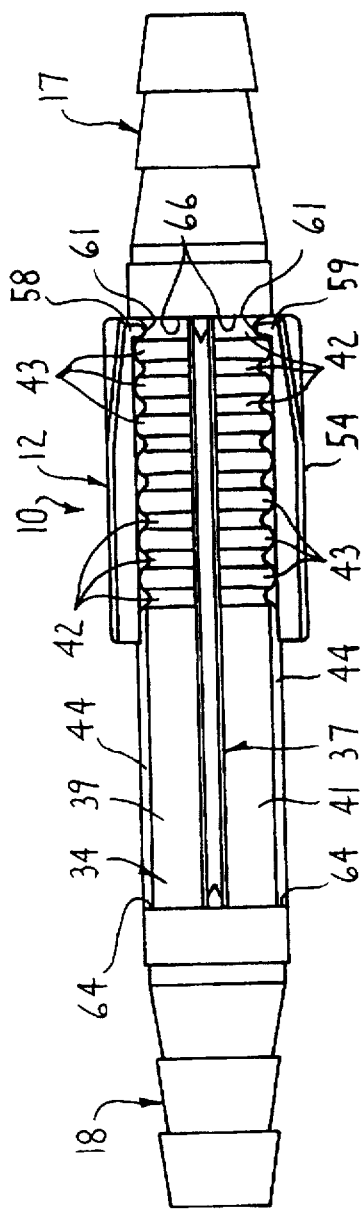
FIG. 4 is a bottom view of the suction regulator.

The cylindrical hollow body 11 includes a guideway, here a reduced diameter recess 34 extending circumferentially over a lower half 33 of the cylindrical body 11 as well as axially over a majority of the length of the hollow body between the tubular feedings 17 and 18. An exterior surface 36 of the reduced diameter recess 34 is semi-cylindrical. A radially outwardly extending fin 37 is provided in the recess 34. The fin 37 is generally planar and extends axially of the hollow body 11 on a side thereof directly opposite from the slot 22. The fin 37 extends radially outwardly to a straight edge 38 that is generally parallel to the longitudinal axis of the hollow body 11. If desired, the edge 38 of the fin 37 can be some structure other than a straight edge in order to better facilitate a gripping of the hollow body 11 by the hand of a user. The fin 38 divides the reduced diameter recess 34 into two sections 39 and 41 as shown in FIG. 4. Each of the sections 39 and 41 includes therein generally one-fourth of the cylindrical surface 36. In other words, the semi-cylindrical surface 36 is divided into two quarter semi-cylindrical surfaces within the sections 39 and 41. The semi-cylindrical surfaces in the sections 39 and 41 directly opposite the slot 22 are smooth and unobstructed as illustrated in FIGS. 1, 2 and 4. This smooth and unobstructed surface covers approximately one-half the axial length of the reduced diameter recess 34. The remaining half of the reduced diameter recess 34 has a plurality of side-by-side grooves 42 therein, each of which function as a stop. In this particular embodiment, eight grooves 42 fill the aforesaid region of the reduced diameter recess 34 adjacent the proximal port 14. Each of the grooves 42 is separated by a rib 43. Further, the grooves 42 and ribs 43 in the respective sections 39 and 41 are laterally aligned with each other and terminate contiguously with the fin 37, but on opposite sides thereof. The difference in radius between the exterior surface 23 on the upper half 21 of the hollow body 11 and the exterior surface 36 in the two sections 39 and 41 is sufficient to define a step or shoulder 44.

The gate member 12 illustrated in FIG. 1 includes a generally semi-cylindrical shell 46 having an exterior semi-cylindrical surface 47 and an interior facing semi-cylindrical surface 48. The thickness of the shell 46 is made greater as at 49 at the lateral edges 51 and 52 of the gate member 12 so as to define an inwardly facing step 53. The edges 51 and 52 extend axially approximately one-half the length of the gate member 12 so that the step 53 terminates at an end of the gate member 12 adjacent the wide end 28 of the slot 22 and at the mid-section 54 of the gate member 12. The edges 56 and 57 of the shell 46 on a side of the mid-section remote from the edges 51 and 52, respectively, are formed into opposing arms 58 and 59 which are contiguous with the thickened or widened edges 49 at the lateral edges 51 and 52 of the shell 46. The arms 58 and 59 are elongated and separated from the remainder part of the shell 46. Each of the arms has a tab 61 at the distal end thereof The exterior surface of each of the tabs 61 conforms to the shape of the bottoms of the grooves 42. In this particular embodiment, the tabs are rounded and the bottoms of the grooves are conformed thereto, namely, they are also rounded to a radius comparable to the rounded radius of the tabs 61.

Figure 8:
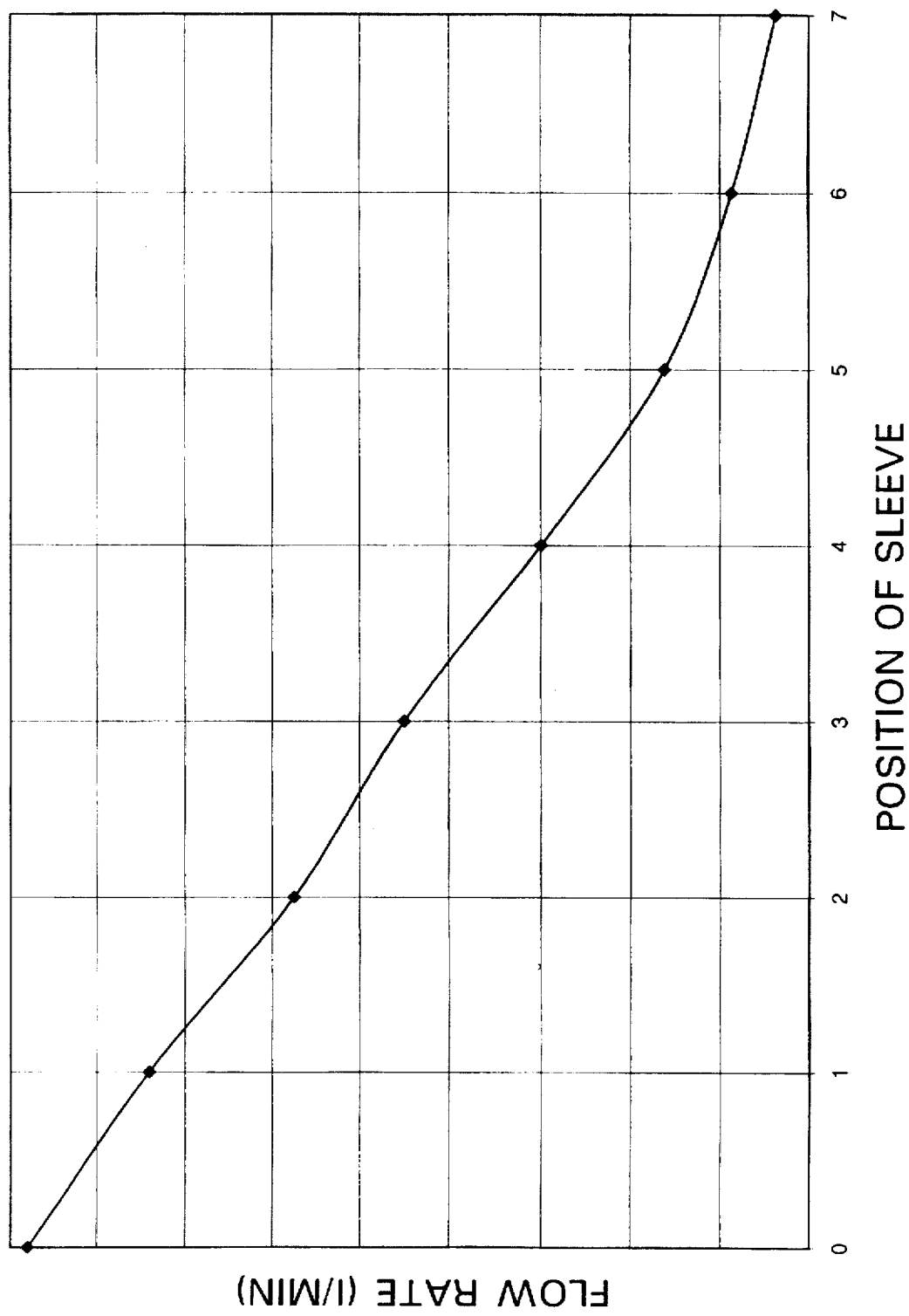
FIG. 8 is a graph showing flow rate vs the position of the gate member relative to the hollow body.

The shell 46 of the gate member 12 is snap fitted onto the hollow body 11 so that the interior surface 48, conforming to the semi-cylindrical surface on the upper half 21 of the hollow body, slidingly engages the exterior surface 23 with minimal clearance therebetween. The upwardly facing step 53 fits beneath the step or shoulder 44 in each of the sections 39 and 41 of the reduced diameter recess 34. The tabs 61 are received into a selected one of the grooves 42. Even the length of the inside edges of the arms 58 and 59 are oriented under the step 44. In the drawings, the tab 61 is received in the rightmost groove or stop 42 adjacent the proximal port 14. The right end of the gate member 12 is abutted against a stop 62 provided on the exterior surface 23 of the hollow body 11. The step 53 overlaps the step or shoulder 44 and the inside edges of the arms 58 and 59 by a distance X illustrated in FIG. 5. As a result, the shell 46 cannot be readily lifted away from the hollow body 11 by reason of the interference fit between the steps 44 and 53. In addition, the steps 44 and 53 serve to guide the gate member 12 leftwardly and rightwardly along the length of the hollow body 11, particularly leftwardly until the left end 63 of the widened edge 49 of the shell 46 of the gate member 12 abuts against a step 64 at the left end of the reduced diameter recess 34. Similarly, the gate member can slide rightwardly along the length of the hollow body 11 until the distal ends of the arms 58 and 59 engage the step 66 at the right end of the reduced diameter recess 34. It will be noted that when the distal ends of the arms 58 and 59 engage the steps 66, the end 63 of the gate member 12 is spaced to the right of the wide end 28 of the slot 22. Thus, when the proximal port 14 is connected to a vacuum source via tubing 19 (FIG. 7), air will be allowed to quietly enter the slot 22 in an unobstructed manner thereby causing the suction rate at the distal port 16 to be near zero (position 7 shown in FIG. 8). As the gate member 12 is moved to the left from the position illustrated in the drawings, the interior surface 48 of the shell 46 of the gate member 12 will begin to cover the wide end 28 of the slot 22 to thereby partially obstruct the ability of air to enter the slot 22. As a result, the suction rate at the distal port will begin to increase and continue to increase as the gate member 12 is moved further toward the left. FIG. 8 is a chart illustrating the suction available at the distal port for each of the eight positions represented by the eight grooves in the reduced diameter recess 34. As the gate member 12 moves leftwardly through the eight positions, it will be noted that the suction rate at the distal port increases in a virtual linear fashion thereby providing the user of the suction regulator a greater degree of control of the suction rate.

The suction regulator 10 disclosed herein is adapted to be gripped by the hand of the user with the palm of the hand generally being oriented above the tubular feeding 17 and the fingers gripping below the edge 38 of the fin 37. The edge 38 tends to keep the user's fingers from interfering with the reduced diameter recess 34 and impeding the movement of the gate member 12. The thumb of the user's hand can frictionally engage the exterior surface 47 of the shell 46 of the gate member 12 to effect movement thereof or it can push against a handle 67 provided mid length on the exterior surface 47 of the shell 46 of the gate member 12. The handle is simply a raised set of ribbing 68. It is, of course, recognized that other forms of a handle 67 can be provided on the exterior surface 47 of the shell 46. The thumb of the user's hand can urge the gate member 12 toward and away from the step 64 to control the suction rate available at the distal port 16.

As the tabs 61 are received into selected grooves or stops 42, the user will feel a tactile sensation caused by the spring action of the arms drawing the gate member to its resting place with the tabs 61 being centered in the grooves. The user will need to impart an axial force to the gate member 12 to cause the tabs to be drawn out of the grooves ride up and over the ribs 43 so that the spring action of the arms 58 and 59 will draw the gate member to the final resting place for the next position.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A suction regulator, comprising:

an elongated hollow body having distal and proximal ports at opposite ends thereof adapted to be connected to an end of a flexible conduit, the proximal port being adapted for conduit connection to a vacuum source and the distal port being adapted for conduit connection to a device needing suction control;

means defining an elongated slot extending from an exterior surface of and through a wall of said hollow body, said slot having a wide end and a narrow end and converging side walls extending over a majority of a length of said slot and from said wide end to said narrow end in a first axial direction of said hollow body;

an elongated axially extending guideway on said hollow body; and a gate member and a guide means thereon operatively guided by said guideway for guiding said gate member axially relative to said hollow body between a first position wherein said gate member is oriented spaced from said wide end of said slot so as to provide unobstructed access to said slot to thereby effect a minimum suction rate at said distal port and a second position fully obstructing access to said slot to thereby effect a maximum suction rate at said distal port.

2. A suction regulator, comprising:

an elongated hollow body having distal and proximal ports at opposite ends thereof adapted to be connected to an end of a flexible conduit, the proximal port being adapted for conduit connection to a vacuum source and the distal port being adapted for conduit connection to a device needing suction control;

means defining an elongated slot extending from an exterior surface of and through a wall of said hollow body, said slot having a wide end and a narrow end and converging side walls extending over a majority of a length of said slot and from said wide end to said narrow end in a first axial direction of said hollow body;

an elongated axially extending guideway on said hollow body;

a gate member and a guide means thereon operatively guided by said guideway for guiding said gate member axially relative to said hollow body between a first position wherein said gate member is oriented spaced from said wide end of said slot so as to provide unobstructed access to said slot to thereby effect a minimum suction rate at said distal port and a second position fully obstructing access to said slot to thereby effect a maximum suction rate at said distal port;

a plural array of side-by-side stops provided along an axial length dimension of said guideway; and said guide means including elastically yieldable tab means operatively engaged with a selected one of said stops to yieldably hold said gate member fixed with respect to said hollow body at selected positions between said first and second positions to effect a suction rate at said distal port that is intermediate said minimum and maximum suction rates.

3. The suction regulator according to claim 2, wherein each of said plural stops, except for the stops located at opposite axial ends of said side-by-side array of said stops, correspond to a specific suction rate that is linearly related to mutually adjacent ones of said stops and from one axial end of said array to the other.

4. The suction regulator according to claim 2, wherein said plural stops are each defined by a depression in an exterior surface of said wall of said hollow body; and wherein said yieldable tab means includes a pair of tabs located on opposite sides of said hollow body and biased arms connecting said tabs to said gate member, said biased arms continuously urging said tabs into said depressions to hold said gate member fixed with respect to said hollow body but also yieldable in response to a manually applied axially directed force to said gate member to cause said tabs to move out of one depression against the urging of said biased arms and into a next adjacent depression so as to provide a tactile sensation to the user.

5. The suction regulator according to claim 2, wherein said hollow body includes an outwardly and axially extending fin that extends co-extensively with said guideway, said fin terminating at an outward extent in an edge so that a user's hand gripping the circumference of said hollow body will also grip said edge to thereby space the user's hand from said stops in said guideway and otherwise prevent interference with the axial movement of said gate member relative to said hollow body at a time that the user simultaneously manually applies an axially directed force to said gate member.

6. A suction regulator, comprising:

an elongated hollow body having distal and proximal ports at opposite ends thereof adapted to be connected to an end of a flexible conduit, the proximal port being adapted for conduit connection to a vacuum source and the distal port being adapted for conduit connection to a device needing suction control;

means defining an elongated slot extending from an exterior surface of and through a wall of said hollow body, said slot having a wide end and a narrow end and converging side walls extending over a majority of a length of said slot and from said wide end to said narrow end in a first axial direction of said hollow body;

an elongated axially extending guideway on said hollow body;

a gate member and a guide means thereon operatively guided by said guideway for guiding said gate member axially relative to said hollow body between a first position oriented spaced from said wide end of said slot so as to provide unobstructed access to said slot to thereby effect a minimum suction rate at said distal port and a second position fully obstructing access to said slot to thereby effect a maximum suction rate at said distal port; and said gate member having a semi-cylindrical shape with semi-cylindrical inwardly and outwardly facing surfaces, said inwardly facing surface conforming to said exterior surface of said hollow body in a region surrounding said slot and slidingly engaging said exterior surface.

7. The suction regulator according to claim 6, wherein said gate member further includes inwardly extending flanges at opposite circumferential ends of said semi-cylindrical gate member.

8. The suction regulator according to claim 7, wherein said guideway comprises axially elongated recesses on opposite sides of said hollow body and into which is received a respective one of said flanges so that said gate member is prevented from moving radially with respect to said hollow body while simultaneously being able to move axially of said hollow body.

9. The suction regulator according to claim 8, wherein said gate member is made of an elastically yieldable material to facilitate insertion, during assembly, of said flanges into said recesses.

10. The suction regulator according to claim 8, wherein a plural array of side-by-side stops is provided along an axial length dimension of each of said recesses; and wherein said guide means includes yieldable tab means operatively engaged with a selected one of said stops to yieldably hold said gate member fixed with respect to said hollow body at selected positions between said first and second positions to effect a suction rate at said distal port that is intermediate said minimum and maximum suction rate.

11. The suction regulator according to claim 10, wherein each of said plural stops, except for the stops located at opposite axial ends of said side-by-side array of said stops, correspond to a specific suction rate that is linearly related to mutually adjacent ones of said stops and from one axial end of said array to the other.

12. The suction regulator according to claim 10, wherein said plural stops are each defined by a groove in an exterior surface of said wall of said hollow body; and wherein said yieldable tab means includes a pair of tabs located on opposite sides of said hollow body and biased arms connecting said tabs to said gate member, said biased arms continuously urging said tabs into said groove to hold said gate member fixed with respect to said hollow body but also yieldable in response to a manually applied axially directed force to said gate member to cause said tabs to move out of one groove against the urging of said biased arms and into a next adjacent groove so as to provide a tactile sensation to the user.

13. The suction regulator according to claim 10, wherein said hollow body includes an outwardly and axially extending fin that extends co-extensively with said guideway, said fin terminating at an outward extent in an edge so that a user's hand gripping the circumference of said hollow body will also grip said edge to thereby space the user's hand from said stops in said guideway and otherwise prevent interference with the axial movement of said gate member relative to said hollow body at a time that the user simultaneously manually applies an axially directed force to said gate member.

14. The suction regulator according to claim 1, wherein said wide end of said slot is curved about a first uniform radius having a centerpoint located within said slot.

15. The suction regulator according to claim 14, wherein said narrow end of said slot is curved about a second uniform radius having a centerpoint located within said slot.

16. The suction regulator according to claim 1, wherein said suction regulator is a surgical suction regulator.

17. The suction regulator according to claim 1, wherein said gate member includes means defining a handle.

18. A suction regulator, comprising:

an elongated hollow body having distal and proximal ports at opposite ends thereof adapted to be connected to an end of a flexible conduit, the proximal port being adapted for conduit connection to a vacuum source and the distal port being adapted for conduit connection to a device needing suction control;

means defining an elongated slot extending from an exterior surface of and through a wall of said hollow body, said slot having a wide end and a narrow end and converging side walls extending over a majority of a length of said slot and from said wide end to said narrow end in a first axial direction of said hollow body;

an elongated axially extending guideway on said hollow body;

a gate member and a guide means thereon operatively guided by said guideway for guiding said gate member axially relative to said hollow body between a first position wherein said gate member is oriented spaced from said wide end of said slot so as to provide unobstructed access to said slot to thereby effect a minimum suction rate at said distal port and a second position fully obstructing access to said slot to thereby effect a maximum suction rate at said distal port; and said hollow body including means defining an abutment against which said gate member is moved to define said first position.

19. The suction regulator according to claim 1, wherein said hollow body has a central, axial extending bore therethrough into which said slot opens, said bore having a constant diameter and a continuous and unobstructed smooth surface between the distal and proximal ports thereof.

20. The suction regulator according to claim 1, wherein said hollow body and said gate member include means for providing a tactile sensation to the user's hand gripping said hollow body and gate member to indicate to the user that the gate member is in a selected position relative to said slot.

21. The suction regulator according to claim 1, wherein said side walls are straight over a majority of the length of said slot.

22. The suction regulator according to claim 21, wherein said straight side walls each have an air noise control means thereon for reducing air noise as air flows thereover.

23. A suction regulator, comprising:

an elongated hollow body having distal and proximal ports at opposite ends thereof adapted to be connected to an end of a flexible conduit, the proximal port being adapted for conduit connection to a vacuum source and the distal port being adapted for conduit connection to a device needing suction control;

means defining an elongated slot extending from an exterior surface of and through a wall of said hollow body, said slot having a wide end and a narrow end and converging side walls extending over a majority of a length of said slot and from said wide end to said narrow end in a first axial direction of said hollow body;

an elongated axially extending guideway on said hollow body;

a gate member and a guide means thereon operatively guided by said guideway for guiding said gate member axially relative to said hollow body between a first position wherein said gate member is oriented spaced from said wide end of said slot so as to provide unobstructed access to said slot to thereby effect a minimum suction rate at said distal port and a second position fully obstructing access to said slot to thereby effect a maximum suction rate at said distal port;

said side walls each having an air noise control means thereon for reducing air noise as air flows thereover, said air noise control means including a smooth and rounded convex surface.

24. A suction regulator, comprising:

an elongated hollow body having distal and proximal ports at opposite ends thereof adapted to be connected to an end of a flexible conduit, the proximal port being adapted for conduit connection to a vacuum source and the distal port being adapted for conduit connection to a device needing suction control;

means defining an elongated slot extending from an exterior surface of and through a wall of said hollow body, said slot having a wide end and a narrow end and converging side walls extending over a majority of a length of said slot and from said wide end to said narrow end in a first axial direction of said hollow body;

an elongated axially extending guideway on said hollow body;

a gate member and a guide means thereon operatively guided by said guideway for guiding said gate member axially relative to said hollow body between a first position wherein said gate member is oriented spaced from said wide end of said slot so as to provide unobstructed access to said slot to thereby effect a minimum suction rate at said distal port and a second position fully obstructing access to said slot to thereby effect a maximum suction rate at said distal port; and all walls of said slot having an air noise control means thereon for reducing air noise as air flows thereover.

25. The suction regulator according to claim 24, wherein said air noise control means includes a smooth and rounded convex surface.

26. The suction regulator according to claim 1, wherein a plurality of stops are provided on said hollow body to yieldably obstruct a movement of said gate member at successive positions intermediate said first and second positions, each of said stops being configured on said hollow body to effect a corresponding successive obstructing of said slot by said gate member so that said successive positions cause at said distal port a generally linear variance of the suction rate as said gate member moves between said first and second positions.

27. The suction regulator according to claim 26, wherein said slot is defined by straight converging side walls.

28. The suction regulator according to claim 27, wherein said wide end of said slot is curved about a first uniform radius having a centerpoint located within said slot.

29. The suction regulator according to claim 28, wherein said narrow end of said slot is curved about a second uniform radius having a centerpoint located within said slot.

* * * * *